United States Patent [19]

Schwalm et al.

[11] Patent Number: 5,191,124

[45] Date of Patent: Mar. 2, 1993

[54] SULFONIUM SALTS HAVING ACID-LABILE GROUPS

[75] Inventors: Reinhold Schwalm, Wachenheim; Andreas Boettcher, Nussloch, both of Fed. Rep. of Germany

[73] Assignee: BASF Aktiengesellschaft, Ludwigshafen, Fed. Rep. of Germany

[21] Appl. No.: 214,011

[22] Filed: Jun. 30, 1988

[30] Foreign Application Priority Data

Jul. 1, 1987 [DE] Fed. Rep. of Germany ....... 3721740

[51] Int. Cl.$^5$ ............................................. C07C 69/96
[52] U.S. Cl. ..................................... 568/18; 558/268; 558/270; 558/260; 549/79
[58] Field of Search ................... 568/18, 6, 13, 15, 39, 568/41, 56, 74, 75, 77; 520/130, 138, 141, 142, 9, 10; 558/263, 270, 260; 556/64, 12, 13, 427; 549/3, 4, 6, 78, 79

[56] References Cited

U.S. PATENT DOCUMENTS

| | | | |
|---|---|---|---|
| 3,159,682 | 12/1964 | Baird et al. | 568/18 |
| 3,359,322 | 12/1967 | Ratts | 568/18 |
| 3,502,710 | 3/1970 | Hatch | 568/18 X |
| 3,739,012 | 6/1973 | Ratts | 568/18 |
| 4,058,400 | 11/1977 | Crivello | 568/18 U X |
| 4,093,663 | 6/1978 | Harris et. al. | 568/18 |
| 4,161,478 | 7/1979 | Crivello | 568/18 X |
| 4,689,288 | 8/1987 | Buiguez et al. | 556/64 U X |
| 4,689,289 | 8/1987 | Crivello | 568/18 U X |
| 4,734,444 | 3/1988 | Henne et al. | 556/69 |
| 4,760,013 | 7/1988 | Hacker et al. | 568/18 U X |
| 4,883,740 | 11/1989 | Schwalm et al. | 556/64 U X |
| 4,933,377 | 6/1990 | Saeva et al. | 556/64 |

Primary Examiner—Paul F. Shaver
Attorney, Agent, or Firm—Herbert B. Keil

[57] ABSTRACT

Sulfonium salts of the general formula

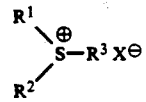

where $R^1$, $R^2$ and $R^3$ are identical or different and are aliphatic and/or aromatic radicals which may contain heteroatoms, or two of the radicals $R^1$ and $R^3$ are bonded to one another to form a ring, with the proviso that one or more of the radicals $R^1$ to $R^3$ contain one or more acid-cleavable groups, or one of the radicals $R^1$ to $R^3$ is bonded to one or more further sulfonium salt radicals, if desired via acid-cleavable groups, and $X^\ominus$ is a non-nucleophilic counter-ion, are suitable as photoinitiators for cationic polymerization.

11 Claims, No Drawings

SULFONIUM SALTS HAVING ACID-LABILE GROUPS

The present invention relates to novel sulfonium salts which, in addition to the sulfonium group, contain acid-labile groups. These compounds produce, under the action of radiation, an acid which eliminates the acid-labile groups and thus dramatically changes the solubility behavior of the compounds. The compounds are particularly suitable as photoinitiators for cationic polymerization and as initiators in photoresists.

Sulfonium salts have long been known in the literature, for example H. M. Pitt, U.S. Pat. No. 2,807,648 (1957); W. Hahn and R. Stroh, U.S. Pat. No. 2,833,827 (1958); G. H. Wiegand and W. E. McEwen, J. Org. Chem. 33 (1968), 2671.

Suitable photoinitiators are virtually exclusively sulfonium salts having complex, non-nucleophilic counter-ions, such as the photoinitiators for cationic polymerization, which were developed by Crivello (e.g. U.S. Pat. Nos. 4,058,400 and 4,058,401). An overview of the use of onium salts in cationic polymerization is given by Crivello in Cationic Polymerization—Iodonium and Sulfonium Salt Photoinitiators, Advances in Polym. Sci. 62 (1984), 1-48.

The use of onium salts in photoresist materials is described in, for example, Possibilities for Photo-imaging Using Onium Salts, Crivello in Corporate Research and Development, General Electric, Schenectady, N.Y. (1983) and by Ito and Willson in Org. Ctgs. and App. Polym. Sci. Proc. 48 (1983), 60 and U.S. Pat. No. 4,491,628.

The sulfonium salts described to date are very effective polymerization initiators or effective acid donors in photoresist materials; however, none of the known sulfonium salts contains acid-labile groups which can be eliminated by the action of radiation and dramatically change the solubility behavior of the compounds.

It is an object of the present invention to provide photoinitiators which have high sensitivity, ideally are effective within a wide range of the spectrum of electromagnetic waves and dramatically change their solubility behavior through exposure.

We have found surprisingly that this object is achieved with specific sulfonium salts which, in addition to the sulfonium group, contain in the same molecule acid-labile groups.

The present invention accordingly provides sulfonium salts of the general formula (I)

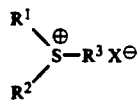

where $R^1$, $R^2$ and $R^3$ are identical or different and are aliphatic and/or aromatic radicals which may contain heteroatoms, or two of the radicals $R^1$ to $R^3$ are bonded to one another to form a ring, with the proviso that one or more of the radicals $R^1$ to $R^3$ contain one or more acid-cleavable groups, and one of the radicals $R^1$ to $R^3$ can be bonded to one or more further sulfonium salt radicals, if desired via acid-cleavable groups, and $X^\ominus$ is a non-nucleophilic counter-ion.

The sulfonium salts preferably contain tert-butoxycarbonyl groups and/or trialkylsilyl groups as acid-cleavable groups.

The novel sulfonium salts can contain one or more acid-cleavable groups per molecule.

The compounds according to the invention are sensitive to short-wavelength UV radiation, electron radiation and X-rays.

The present invention also provides a process for the preparation of the novel sulfonium salts, wherein hydroxyphenylsulfonium salts having non-nucleophilic counter-ions are esterified or etherified at the phenolic function in a conventional manner.

Particularly suitable counter-ions are complex non-nucleophilic metal halides.

The sulfonium salts having complex counter-ions produce, under the action of radiation, a strong acid which eliminates the acid-labile group and converts the alkali-insoluble substances into base-soluble phenolic compounds.

Since the elimination reactions are catalytic, the acid is not consumed but can initiate further reactions, such as the polymerization of cationically polymerizable monomers or the elimination of acid-labile groups, as, for example, in polyacetals or poly-tert-butyl methacrylate. The novel sulfonium salts change their solubility behavior so that they subsequently become capable of being washed out with an aqueous alkaline medium.

In the general formula (I) for the novel sulfonium salts

$R^1$, $R^2$ and $R^3$ may be identical or different and are each an aliphatic radical, such as alkyl of 1 to 12, preferably 1 to 6, carbon atoms, e.g. methyl, ethyl, n-propyl, isopropyl, n-butyl, isobutyl, tert-butyl, pentyl or hexyl, a cycloaliphatic radical, e.g. cyclohexyl or cyclopentyl, each of which may be substituted, or aryl, e.g. phenyl or naphthyl, or are each aryl which is substituted by 1 to 4 alkyl groups of 1 to 6, preferably 1 to 4, carbon atoms, alkoxy of 1 to 4, preferably 1 to 3, carbon atoms, 1 or 2 halogen atoms, such as fluorine, chlorine or bromine, for example methylphenyl, methoxyphenyl, chlorophenyl, bromophenyl, dichlorophenyl or dimethylphenyl, or two of radicals $R^1$ to $R^3$ may be bonded to one another to form a ring, in particular a 5-membered or 6-membered ring, and one or more of the radicals $R^1$ to $R^3$ contain one or more acid-cleavable groups.

Examples of sulfonium salts of the general formula (I) in which $R^3$ is, for example, 4-tert-butoxycarbonyloxyphenyl, 4-tert-butoxycarbonyloxy-3,5-dimethylphenyl, 4-tert-butoxycarbonyloxy-3-methylphenyl, 4-tert-butoxycarbonyloxy-2-methylphenyl, 4-tert-butoxycarbonyloxy-3,5-dimethoxyphenyl, 4-tert-butoxycarbonyloxy-3,5-diphenylphenyl, 4-tert-butoxycarbonyloxy-1-naphthyl, 4-trimethylsilyloxyphenyl or 4-trimethylsilyloxy-1-naphthyl, or those in which $R^1$ and $R^2$, for example, form a tetramethylene bridge and $R^3$ has the same meanings as above:

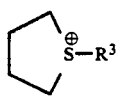

or compounds in which $R^1$ is methyl, $R^2$ is phenyl or tolyl and $R^3$ is a substituted phenyl derivative having acid-cleavable groups, for example

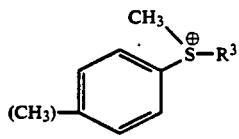

where $R^3$ is, for example, 4-tert-butoxycarbonyloxyphenyl, 2,4-di-tert-butoxycarbonyloxyphenyl, 4-tert-butoxycarbonyloxy-2-methoxy-phenyl or 4-trimethylsilylphenyl, or where $R^1$ is phenyl or $C_1$–$C_{12}$-substituted phenyl or halogen-substituted phenyl and $R^2$ and $R^3$ are each a substituted phenyl derivative having acid-cleavable groups, for example

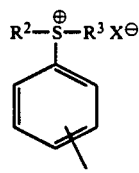

where $R^2$ and $R^3$ are each, for example, 4-tert-butoxycarbonyloxyphenyl, 4-trimethylsilyloxyphenyl, 4-tert-butyldimethylsilyloxyphenyl or 4-tert-butoxycarbonyloxy-3,5-dimethylphenyl, or $R^1$, $R^2$ and $R^3$ are identical, i.e. sulfonium salts which contain three of these radicals having acid-cleavable groups.

Other suitable compounds are those of the general formula (I) where one of the radicals $R^1$ to $R^3$ is bonded to one or more further sulfonium salt radicals, if desired via acid-cleavable groups, the said compounds thus likewise having a plurality of sulfonium groups in the molecule, for example

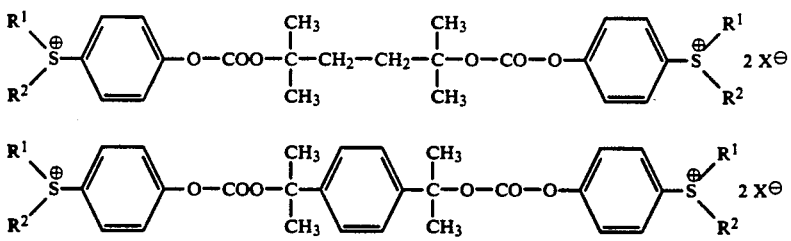

Other examples of sulfonium salts according to the invention are listed below:

where $X^\ominus$ is halogen or, preferably, a complex anion, such as $BF_4^\ominus$, $AsF_6^\ominus$, $SbF_6^\ominus$ or $PF_6^\ominus$, $R^1$ and $R^2$ are each, as started above, alkyl or unsubstituted or substituted aryl or are bonded to one another to form a ring (i.e. divalent, e.g. tetramethylene), $R^4$ is tert-butoxycarbonyl or trialkylsilyl, e.g. trimethylsilyl or tert-butyldimethylsilyl.

Regarding the preparation of the novel sulfonium salts, the following may be stated:

The sulfonium salts according to the invention can be prepared by conventional methods of organic chemistry for the synthesis of esters, carbonates and ethers, by starting from known sulfonium salts having phenolic groups and reacting these in such a way that tert-butyl esters, tert-butyl carbonates or silyl ethers of phenols are formed.

According to the invention, a process for the synthesis of the compounds having acid-labile carbonate or ester groups is proposed, in which a hydroxyphenylsulfonium salt with a non-nucleophilic counter-ion is treated with a base and then reacted with an activated carbonyl compound. The acid-labile silyl groups are introduced by reacting the stated hydroxyphenylsulfonium salt with a conventional silylating reagent, such as hexamethyldisilazane or a silyl chloride.

Hydroxyphenyldialkylsulfonium salts which already contain a non-nucleophilic counter-ion can be prepared, for example, by a synthesis method in J. Polym. Sci., Chem. Ed. 18 (1980), 1021. In the novel process, preferably potassium tert-butylate in dry tetrahydrofuran is added to these sulfonium salts, after which a solution of di-tert-butyl dicarbonate in tetrahydrofuran (THF) is added drop-wise. Working up and recrystallization give the pure sulfonium salts.

Alternatively, the hydroxyphenyldialkylsulfonium salts can be reacted with activated carbonyl compounds, e.g. tert-butoxycarbonyl-N-imidazole.

Bis-(hydroxyphenyl)-arylsulfonium salts can be prepared, for example, by the method due to Crivello in J. Polym. Sci., Chem. Ed. 18 (1980), 2697, by reacting a diaryliodonium salt having a non-nucleophilic counterion with, for example, a bis-(hydroxyphenyl) sulfide, the reaction being catalyzed by copper(II). The sulfonium salts thus prepared can likewise be converted into the derivatives with carbonate, ester or ether groups.

Tris-(hydroxyphenyl)-sulfonium salts can be prepared, for example, by a synthesis method from U.S. Pat. No. 2,833,827 (1958) and can be converted to derivatives similarly to the stated process according to the invention.

The novel sulfonium salt, phenylbis-(tert-butoxycarbonyloxyphenyl)-sulfonium hexafluoroarsenate, is used as an example to show that the hydrophobic, alkali-insoluble starting compound can be converted into the phenolic derivative by exposure and a subsequent heating step.

Use of the sulfonium salts as photoinitiators for the elimination of acid-labile side groups in photoresist materials can be demonstrated by applying a photoresist solution of poly-(tert-butyl methacrylate) and 20% by weight, based on the polymer, of a novel sulfonium salt to a silicon wafer by spin coating, and carrying out imagewise irradiation, heating and development. The exposed parts can be completely removed using an alkaline developer, whereas no removal of material takes place in the unexposed parts. If the triarylsulfonium salts usually used are employed, a thin residual layer remains behind and a cosolvent is required to dissolve the sulfonium salts to achieve clean development.

In the Examples which follow, parts and percentages are by weight, unless stated otherwise.

EXAMPLE 1

Preparation of dimethyl-4-tert-butoxycarbonyloxyphenylsulfonium hexafluoroarsenate Dimethyl-4-hydroxyphenylsulfonium hexafluoroarsenate is prepared by the synthesis method in J. Polym. Sci., Polym. Chem. Ed. 18 (1980), 1021. The sulfonium chloride is first obtained from phenol and dimethyl sulfoxide in methanol while passing through dry HCl, and the said salt is converted into dimethyl-4-hydroxyphenylsulfonium hexafluoroarsenate in a subsequent metathesis reaction with potassium hexafluoroarsenate.

2.0 parts of this salt are dissolved in 55 parts of dry tetrahydrofuran while passing through $N_2$. 1 part of potassium tert-butylate is then added, after which stirring is carried out for 10 minutes. A solution of 1.27 parts of di-tert-butyl dicarbonate in 10 parts of tetrahydrofuran is added dropwise and stirring is carried out for 1 hour. The reaction mixture is poured into 50 parts of ice water and extracted several times with ethyl acetate. The combined ethyl acetate fractions are dried over magnesium sulfate, and ethyl acetate is then stripped off. The crude product thus obtained is recrystallized twice from ethanol. Pure dimethyl-4-tert-butoxy-carbonyloxyphenylsulfonium hexafluoroarsenate is obtained in a yield of 1.5 parts.

NMR: 1.5 ppm (s, 9H), 3.3 ppm (s, 6H); 7.65 ppm and 8.15 ppm (para-substituted aromatics, each d, 4H)

IR: Ar—O—CO—O—aliph. 1976 cm$^{-1}$

| Elemental analysis | C | H | S | As | F |
|---|---|---|---|---|---|
| Found | 35.0 | 4.3 | 7.6 | 16.7 | 25.4 |
| Calculated | 35.1 | 4.3 | 7.2 | 16.9 | 25.7 |

Dimethyl-4-tert-butoxycarbonyloxyphenylsulfonium hexafluoroarsenate is also obtained by reacting dimethyl-4-hydroxyphenylsulfonium hexafluoroarsenate (3.3 parts) with tert-butyl imidazole-N-carboxylate (1.9 parts) in 15 parts of tetrahydrofuran. The reaction mixture is heated for 8 hours at 70° C. and then cooled, after which the tetrahydrofuran is distilled off and the residue is recrystallized from ethanol.

Other salts, such as hexafluoroantimonate and hexafluorophosphate, can also be prepared in a similar manner.

EXAMPLE 2

Synthesis of phenylbis-(4-tert-butoxycarbonyloxyphenyl)sulfonium hexafluoroarsenate 11.75 g (0.025 mole) of diphenyliodonium hexafluoroarsenate, 5.46 g (0.025 mole) of 4,4'-dihydroxydiphenylsulfide and 0.2 g of copper(II) acetate are initially taken in a 100 ml two-necked flask equipped with reflux condenser and magnetic stirrer, while passing through $N_2$. The mixture is heated for 3 hours at 125° C. under $N_2$, and is then poured into a beaker and extracted several times with diethyl ether. The crude product is recrystallized from chloroform/diethyl ether. The yield is 6.3 g. NMR and IR spectra show that the newly prepared product is phenylbis-(4-hydroxyphenyl)sulfonium hexafluoroarsenate.

6.3 g of the synthesized phenylbis-(4-hydroxyphenyl)sulfonium hexafluoroarsenate are dissolved in 100 ml of dry tetrahydrofuran while passing through $N_2$. 2.9 g of potassium tert-butylate are then added, after which stirring is continued for 10 minutes. 6.24 g of di-tert-butyl dicarbonate in 20 ml of tetrahydrofuran are added dropwise and stirring is continued for a further hour. The reaction mixture is poured into 150 g of ice water and extracted several times with ethyl acetate. The combined ethyl acetate fractions are dried over magnesium sulfate and the solvent is stripped off. Recrystallization gives 7.0 g of pure phenylbis-(4-tert-butoxycarbonyloxyphenyl)-sulfonium hexafluoroarsenate.

NMR: 1.5 ppm (s, 18H); 7.5 ppm (d, 4H); 7.7 ppm (m, 5H); 7.8 ppm (d, 4H)

IR: (C=O, carbonate) 1760 cm$^{-1}$

Melting point: 128° C.

EXAMPLE 3

Phenylbis-(4-tert-butoxycarbonyloxyphenyl)-sulfonium hexafluoroarsenate is applied to a sodium chloride plate and heated for 30 seconds at 120° C. The IR spectra shows a sharp carbonyl band at 1760 cm$^{-1}$ (carbonate) and no phenolic OH; there is no detectable change compared with the spectrum of the unheated substance. If exposure is now carried out for 10 seconds to excimer laser light of wavelength 248 nm followed by heating for 30 seconds at 120° C., the carbonyl band is found to have completely vanished and an OH band has appeared at 3500 cm$^{-1}$.

The starting material is insoluble in dilute sodium carbonate solution whereas a product treated according to the above Example dissolves completely in this alkaline solvent.

EXAMPLE 4

Synthesis of 4-(1-trimethylsilyloxynaphthyl)-tetrahydrothiophenium chloride 5.33 g (20 moles) of 4-(1-hydroxynaphthyl)-tetrahydrothiophenium chloride are initially taken and 2.4 ml of hexamethyldisilazane are added dropwise at 25° C. in the course of 45 minutes. A further 5 ml of hexamethyldisilazane are added and allowed to react for 7 hours at 100° C. The excess hexamethyldisilazane is distilled off from the resulting yellow solution under reduced pressure from an oil pump. 6.5 g of a yellow oil remain. The NMR spectrum corresponds to that of the expected silylated product.

EXAMPLE 5

A mixture of 30 parts of distilled styrene, 0.5 part of the phenylbis-(tert-butoxycarbonyloxyphenyl)sulfonium hexafluoroarsenate prepared according to Example 2 and 10 parts of tetrachloromethane is exposed to a Cd-Xe lamp for 15 minutes under nitrogen. Exothermic polymerization takes place and the reaction solution becomes viscous. Thereafter, the solution is heated for a further 30 minutes at about 80° C., diluted, extracted by shaking with dilute carbonate solution and precipitated in methanol. The IR spectrum shows that the product is pure polystyrene and that no phenol absorption of the decomposed initiator is present.

EXAMPLE 6

Commercial poly-(tert-butyl methacrylate) ($\overline{M}_n$ 83,000) is dissolved in methylglycol acetate and the solution is mixed with 20%, based on poly-(tert-butyl methacrylate), of dimethyl-4-tert-butoxycarbonyloxyphenylsulfonium hexafluoroarsenate, so that a solution having a total solids content of 25% is obtained. This solution is filtered through a filter having a pore diameter of 0.2 μm and applied to a silicon wafer by spin coating at 3,000 rpm. The film is heated for 5 minutes at 90° C., exposed imagewise through a quartz mask and then heated for 1 minute at 120° C. The exposed parts can be completely developed with an alkaline developer of pH 13.0.

In a comparative experiment with triphenylsulfonium hexafluoroarsenate instead of the novel sulfonium salt, a residual layer of about 0.1 μm remained on the wafer in the exposed parts.

We claim:

1. A sulfonium salt of the formula (I)

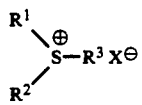

where $R^1$, $R^2$ and $R^3$ are identical or different and are each an aliphatic or aromatic radical or an aliphatic and aromatic radical which contain heteroatoms, or two of the radicals $R^1$ to $R^3$ are bonded to one another to form a ring, with the proviso that at least one of the radicals $R^1$ to $R^3$ contain one or more acid-cleavable groups bonded to oxyphenyl or oxynaphthyl, and one of the radicals $R^1$ to $R^3$ can be bonded to one or more further sulfonium salt radicals and $X^\ominus$ is a non-nucleophilic counter-ion.

2. A sulfonium salt of claim 1, wherein the acid-cleavable group is tert-butoxycarbonyl.

3. A sulfonium salt of claim 1, wherein the acid-cleavable group is trialkylsilyl.

4. A sulfonium salt of claim 1, which contains one acid-cleavable group per molecule.

5. A sulfonium salt of claim 2, which contains one acid-cleavable group per molecule.

6. A sulfonium salt of claim 3, which contains one acid-cleavable group per molecule.

7. A sulfonium salt as claimed in claim 1, which contains two acid-cleavable groups per molecule.

8. A sulfonium salt of claim 2, which contains two acid-cleavable groups per molecule.

9. A sulfonium salt of claim 3, which contains two acid-cleavable groups per molecule.

10. A sulfonium salt as claimed in claim 1, which contains three acid-cleavable groups per molecule.

11. A sulfonium salt of claim 1 wherein one or more of the radicals $R^1$ to $R^3$ is bonded to one or more further sulfonium salt radicals via acid-cleavable groups.

* * * * *